United States Patent [19]

Härle

[11] Patent Number: 5,203,783
[45] Date of Patent: Apr. 20, 1993

[54] OSTEOSYNTHETIC FIXATION AND FORCE TRANSMITTING APPARATUS

[76] Inventor: Anton Härle, Drechslerweg 40, W-4400 Münster-Roxel, Fed. Rep. of Germany

[21] Appl. No.: 697,323

[22] Filed: May 8, 1991

[30] Foreign Application Priority Data

May 10, 1990 [DE] Fed. Rep. of Germany ....... 4014973

[51] Int. Cl.$^5$ .............................................. A61B 17/60
[52] U.S. Cl. ........................................ 606/53; 606/54; 606/58
[58] Field of Search .................................. 606/54-59

[56] References Cited

U.S. PATENT DOCUMENTS

| 2,391,537 | 12/1945 | Anderson | 606/54 |
| 4,488,542 | 12/1984 | Helland | 606/57 X |
| 4,714,076 | 12/1987 | Compte et al. | 606/59 |
| 4,944,743 | 7/1990 | Gotzen et al. | 606/59 X |

FOREIGN PATENT DOCUMENTS

| 0073455 | 4/1986 | European Pat. Off. . |
| 0233930 | 7/1989 | European Pat. Off. . |
| 2708866 | 10/1977 | Fed. Rep. of Germany . |
| 2938202 | 4/1981 | Fed. Rep. of Germany . |

Primary Examiner—Robert A. Hafer
Assistant Examiner—Sam Rimell
Attorney, Agent, or Firm—Peter K. Kontler

[57] ABSTRACT

An osteosynthetic force transmitting and positioning apparatus has two force transmitting members one of which is slidably telescoped into the other and each of which or at least one of which is connected or is connectable to one or more connecting components for bone screws, bone pins and/or other types of fasteners which secure the connectors to discrete bones, to fragments of bones or to osteosynthetic plates. The connections between the force transmitting members and the connecting components are such that the orientation of the fasteners can be altered in the direction of any one of three axes which are disposed at right angles to each other. Such connections can include fulcra, hinges, pivots, pin-and-hole couplings or others.

22 Claims, 2 Drawing Sheets

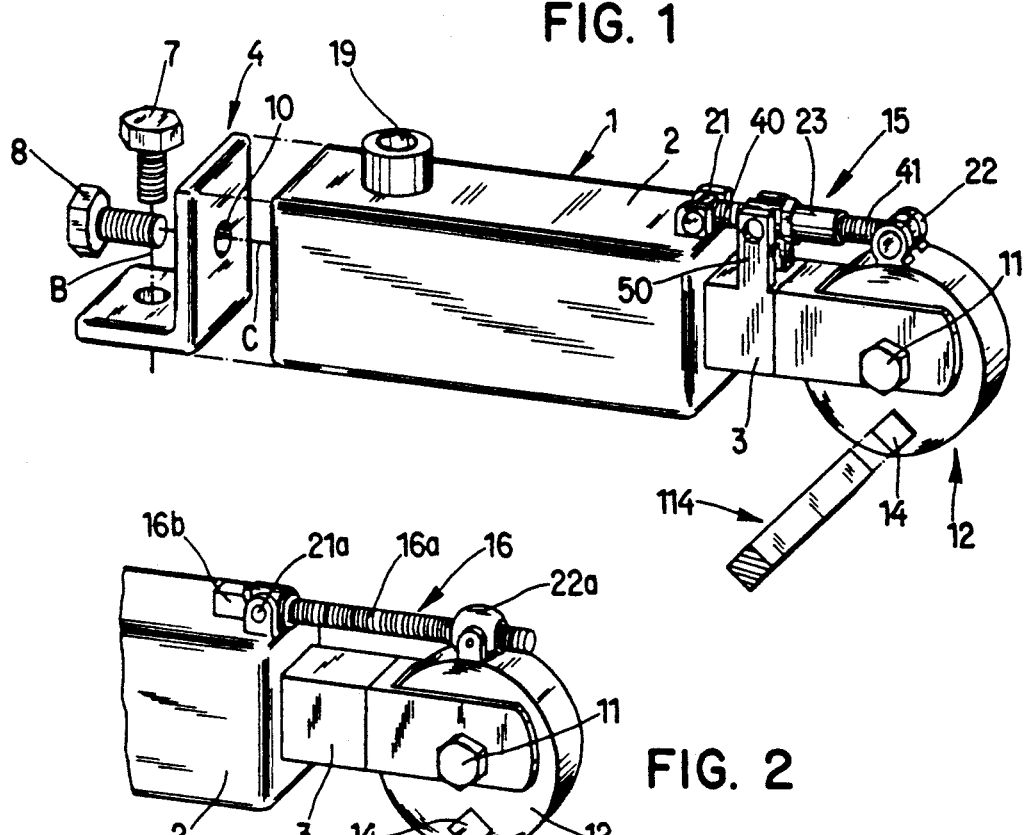
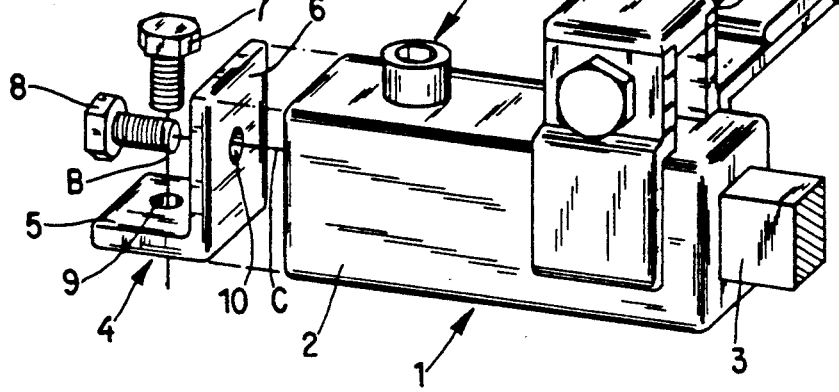
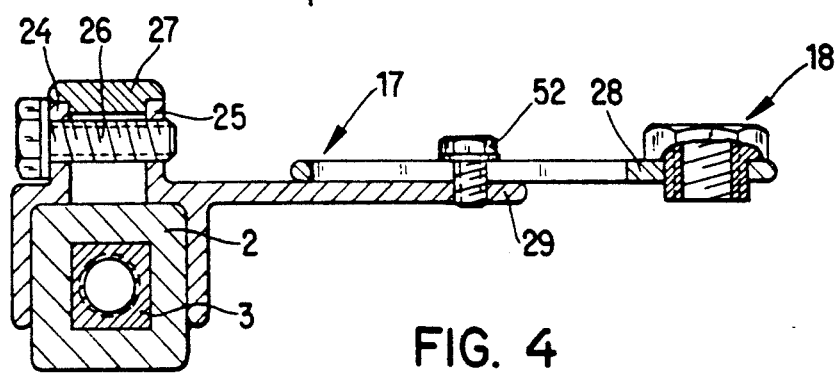

OSTEOSYNTHETIC FIXATION AND FORCE TRANSMITTING APPARATUS

BACKGROUND OF THE INVENTION

The invention relates to osteosynthetic fixation and force transmitting apparatus. More particularly, the invention relates to improvements in apparatus of the type wherein two or more force transmitting members which are movably connected to each other can be directly or indirectly affixed to bones, bone fragments or auxiliary osteosynthetic parts.

Osteosynthesis of tubular bones following fractures or corrective osteotomy invariably or often necessitates the positioning of bones or bone fragments in a predetermined position and/or orientation and subsequent immobilization of the properly positioned and/or oriented bones or bone fragments against any movement until the mending or healing process has progressed sufficiently to warrant removal of the apparatus. The problem of proper fixation of bone fragments and interfragmentary fragment compression is recognized for many years, and many proposals to solve such problem are known in the art. On the other hand, much less attention was devoted to the equally important task of moving the bones and bone fragments to an optimum position or orientation relative to each other.

The task of properly positioning and orienting bones and bone fragments is assigned to osteopaths and other specialists in the bone mending and bone setting field. Thus, it is left to the skill and dexterity of the specialist to properly position and orient the bones or bone fragments in the body of a patient without any, or without adequate, equipment to assist the specialist in the performance of such tasks. Therefore, the results of operations which involve resetting and/or reorienting of bones or bone fragments are often quite unsatisfactory. Moreover, the absence of adequate equipment to assist the specialist necessitate long-lasting operations, incomplete or unsatisfactory repositions following bone fractures and improper orientation of the axes of various mended joints. Improper orientation of the axis of a joint often entails posttraumatic damage to the joint as a result of incongruity of components of the affected joint and/or local overstressing of the cartilage.

Heretofore, a correction of mutual positions of bone fragments was possible only with assistance from external tensioning systems which are designed to permit correction of the position of the axis of a joint subsequent to initial setting by relying on reposition of bone fragments by way of distraction. A drawback of such tensioning systems is that they necessitate external fixation, i.e., the skin must be traversed by threaded bone pins, bone screws or other parts which are driven into bones or bone fragments. This often causes infections at the loci of penetration of fasteners through the skin. Therefore, many health authorities prohibit prolonged external fixation and restrict such mode of fixation only to primary treatments of seriously injured patients for a limited number of days.

Force transmitting apparatus for osteosynthetic purposes are described and shown, by way of example, in German Pats. Nos. 27 08 866 and 29 38 202 and in European Pat. No. B 02 33 930.

European Pat. No. B 0 073 455 discloses a force transmitting apparatus which constitutes a repositional instrumentality for use in internal osteosynthesis. The patented apparatus renders it possible to perform controlled distraction of bone fragments to thus establish the necessary circumstances for correction, namely to overcome the tensioning of soft parts. The patented apparatus is further capable of correcting or compensating for lateral shifting of bone fragments. However, the patented apparatus also exhibits a number of drawbacks. Thus, correction of, or compensation for, lateral shifting of bone fragments can be achieved only by driving the repositioning screw into the soft tissue at the opposite side of the plate. This can result in injuries to blood vessels and nerves.

An important prerequisite for proper repositioning of fractured bones, especially spinal columns but also in connection with corrective osteotomy, is to ensure the carrying out of accurately metered and controlled angular corrections. Such requirements cannot be met by resorting to heretofore known apparatus including the apparatus of European Pat. No. B 0 073 455. Fixation on the osteosynthetic plate has contributed significantly to simplification of osteotomy involving a lengthening of the bones. However, such fixation interferes with bending of the plate which is often necessary for better conformance to the anatomy of a patient.

Corrective treatment involving elimination or reduction of deformities of the spinal column and/or mending of fractured vertebrae preferably involves a first step of correcting the positions and orientation of bone fragments or bone portions prior to fixation to the plate. Such procedure is complex and difficult, mainly due to special anatomical circumstances, i.e., the available space for the application of screws is minimal because the specialist must be concerned with the position of the spinal cord and, therefore, it is possible to use only one bone screw per vertebra. Furthermore, drilling of holes and introduction of the shanks of bone screws into vertebrae through an already applied plate (such as is known from osteosynthesis of extremities) is difficult or impossible because the specialist in charge is likely to damage the spinal cord due to lack of adequate overview of anatomical circumstances in connection with such types of operations. The situation is analogous in connection with complex corrective osteotomies of extremities, particularly in close or immediate proximity to the joints, i.e., it is desirable and advantageous to ensure that a different setting can be inspected and tested without it being necessary to rely on plate fixation. Thus, it is much simpler to inspect the results of the operation and to carry out, if necessary, the required corrective measures. For example, it is possible to carry out such work without transferring bone screws which invariably constitutes a complex, difficult and time-consuming task.

OBJECTS OF THE INVENTION

An object of the invention is to provide an apparatus which can be used by osteotomists and other specialists in the field of mending, resetting, reshaping and similarly treating bones to facilitate the task of properly positioning and orienting bones and/or bone fragments.

Another object of the invention is to provide a highly versatile apparatus which can be used in connection with shortening and lengthening as well as many other corrective undertakings involving bones and bone fragments.

A further object of the invention is to provide an apparatus which can be utilized for highly accurate positioning and orienting of bones or bone fragments in hard-to-reach parts of the anatomy, such as certain extremities and the spinal column.

An additional object of the invention is to provide an apparatus wherein one or more connecting components for two or more adjustable force applying or transmitting members can be adjusted in space in any desired direction and with a high degree of accuracy by performing angular and/or translatory and/or other simple, complex or highly complex movements.

Still another object of the invention is to provide an apparatus which can be utilized to simplify and shorten osteotomic treatment of bones or bone fragments.

A further object of the invention is to provide a simple and compact apparatus which is designed to facilitate the application to and adjustment (such as reorientation) of the spinal column, vertebrae and/or fragments of vertebrae.

Another object of the invention is to provide an apparatus which constitutes an improvement over and a further development of apparatus of the type described and shown in European Pat. No. B 0 073 455.

An additional object of the invention is to provide a novel and improved method of controlledly changing the positions and/or the orientation of bones or bone fragments.

SUMMARY OF THE INVENTION

The invention is embodied in an osteosynthetic bone fixation and force transmitting apparatus which comprises first and second force transmitting members (for example, the first member can be slidably and rotatably or non-rotatably telescoped into the second member or vice versa), means for moving the members relative to each other in a predetermined direction (preferably in a direction to increase or reduce the combined length of the two members), means for at least indirectly connecting the members to at least one bone (e.g., to fragments of a spinal column) comprising at least one connecting element or component which is mounted on one of the members, and a fulcrum for the connecting component. The fulcrum defines a predetermined axis which is substantially normal to the predetermined direction. Thus, the two members can transmit different forces to two discrete bones or to fragments of a particular bone by moving relative to each other in the predetermined direction and/or by changing the angular position of the component about the aforementioned axis.

The component can comprise a bracket having a first leg and a second leg which is or can be normal to the first leg. The second leg can be mounted on the one member, and the fulcrum is connected with the first leg of the bracket. Such apparatus can comprise a second fulcrum which connects the second leg to the one member for angular movement about a second axis which is parallel to the predetermined direction.

The connecting means can further comprise a second connecting component which is mounted on the other member for angular movement about a second axis normal to the predetermined direction and to the predetermined axis. Means can be provided for releasably locking the at least one component and/or the second component in a selected angular position relative to the one member or the other member. The at least one component and/or the second component can be provided with a socket for a bone screw or pin.

The apparatus can further comprise means for changing the angular position of the at least one component and/or the second component, and such position changing means can comprise a feed screw mating with a rotary nut, a rotary spindle which mates with a non-rotatable nut, a worm and worm wheel drive, a helical gear wheel, or any other device which can change the angular position of the at least one component and/or the other component in a predictable and reproducible manner. The position changing means can be connected to the respective component and to one of the two members or to the respective component and each of the two members. Means can be provided for releasably coupling the position changing means to at least one of the two members.

The fulcrum for the at least one component can be provided on the one member, i.e., the at least one component can change its angular position relative to the one member.

The at least one component or another component of the connecting means can extend substantially at right angles to the predetermined direction and can constitute an elongated arm having a first end portion adjacent the first member and a second end portion provided with a socket for a bone pin or bone screw. The arm can be assembled of a plurality of sections including a first section having the first end portion and a second section having the second end portion. The respective connecting component can further comprise means for releasably coupling the sections to each other in any one of a plurality of different positions in each of which the two end portions are disposed at a different distance from each other. The connecting means can further comprise means for securing the first end portion of the arm directly to the first member.

The connecting means can further comprise devices which connect the members to bones, fragments of bones or to plates or other osteosynthetic parts independently of each other.

The at least one component can be connected to the one member by the aforementioned fulcrum or by other means, e.g., by means for articulately connecting the at least one component to the one member. Such means for articulately connecting can include a pin-and-hole connection which enables the at least one component and the one member to pivot relative to each other about an axis which is preferably normal to the predetermined direction and is or can be parallel to the predetermined axis.

Means (such as a hinge) can be provided for securing the at least one component to the one member with freedom of movement about a second axis which is normal to the predetermined direction and to the predetermined axis. The at least one component of connecting means in such apparatus can include a plate having an elongated slot. Such apparatus can further comprise a fastener for the plate, and the plate can be provided with means (e.g., with serrations) for locating the fastener at any one of a plurality of different distances from the hinge.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain presently preferred specific embodiments with reference to the accompanying drawing.

BRIEF DESCRIPTION OF THE DRAWING

FIG. 1 is a perspective view of an apparatus which embodies one form of the invention, one of the two illustrated connecting components being shown in detached position;

FIG. 2 is a fragmentary perspective view of an apparatus which constitutes a modification of the apparatus of FIG. 1;

FIG. 3 is a fragmentary perspective view of a third apparatus wherein a rotary connecting component of the apparatus of FIGS. 1 and 2 is replaced with a connecting component in the form of an elongated arm;

FIG. 4 is a central longitudinal sectional view of the elongated connecting component which is shown in FIG. 3;

DESCRIPTION OF PREFERRED EMBODIMENTS

Figure 7:
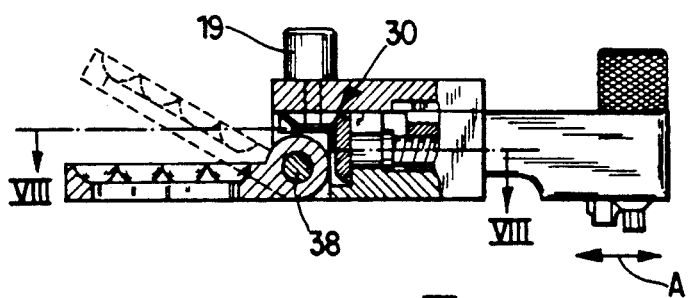
FIG. 7 is a partly side elevational and partly central longitudinal sectional view of the apparatus of FIG. 6, the section being taken in the direction of arrows as seen from the line 7—7 in FIG. 8.
Figure 8:
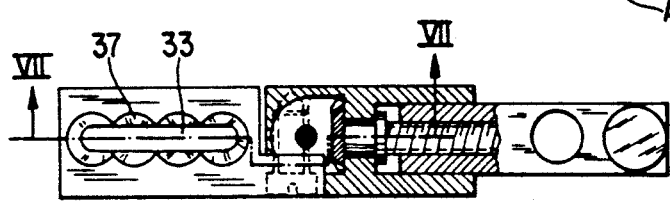
FIG. 8 is a plan view of the apparatus of FIGS. 6 and 7, with certain parts shown in section substantially as seen in the direction of arrows from the line 8—8 in FIG. 7.

The osteosynthetic fixation and force transmitting apparatus 1 which is shown in the drawing constitutes an improvement over and a further development of apparatus which is described and shown in European Pat. No. B-0 073 455. The apparatus 1 comprises two elongated force transmitting members 2 and 3, with the member 3 slidably telescoped into the member 2 for movement in directions indicated by a double-headed arrow A (FIG. 3). The means for moving the members 2, 3 relative to each other (in order to increase or reduce the combined length of these members, as seen in the direction of arrow A) includes a bevel gear transmission 30 which is shown in FIGS. 7 and 8 and includes a rotary element 19 having a polygonal (e.g., hexagonal) socket for the working end of a suitable wrench (not shown) which can rotate the element 19 in a clockwise direction or in a counterclockwise direction, depending on the desired combined length of the members 2 and 3. The member 2 can be said to constitute a housing for the elongated bar- or rod-shaped member 3. It is clear that the means for moving the members 2, 3 relative to each other can depart from the moving means 30 of FIGS. 7 and 8 without departing from the spirit of the invention.

The means for connecting the members 2, 3 to discrete bones, to two fragments of a broken bone, to osteosynthetic plates or to any other parts (not specifically shown) can comprise one or more connecting components including the components 4 and 12 which are shown in FIGS. 1 to 3 and are respectively mounted on the members 2 and 3. The component 4 is a substantially L-shaped bracket having a first leg 5 which extends in parallelism with the longitudinal direction of the members 2, 3 and a second leg 6 which is normal to the leg 5 and is adjacent the exposed end face of the member 2 at a location remote from the connecting component 12. The leg 5 has a hole or bore 9 for the shank of a screw 7 acting as a fulcrum for the bracket 4 and defining a pivot axis B which is normal to the direction indicated by the arrow A. The fulcrum 7 can constitute a bone pin or bone screw (e.g., a screw of the type disclosed in commonly owned copending patent application Ser. No. 07/629,996 filed Dec. 19, 1990 for "Screw for use in osteosynthesis"). Alternatively, the fulcrum 7 can constitute a so-called bone pin or a standard screw which is used to affix the leg 5 to a plate or the like, not shown, forming an auxiliary part of the osteosynthetic apparatus.

The leg 6 has a hole or bore 10 which receives a portion of the shank of a screw 8. Such screw can be said to constitute a second fulcrum which connects the bracket 4 to the member 2 for angular movement about an axis C which is normal to the axis B and is parallel to the direction indicated by the arrow A. If the screw 8 is tightened, the bracket 4 is held against turning about the axis C. Analogously, the screw 7 can be tightened to maintain the bracket 4 (and hence the members 2 and 3) in a selected angular position relative to the axis B. The screw 8 can constitute a standard machine screw, and the screw 7 can be of the type described in the aforementioned commonly owned copending patent application Ser. No. 07/629,996. The apparatus 1 can be fixed to an osteosynthetic tensioning plate but can be used without such a plate, i.e., it can be secured to one or more bones directly by means of pins, screws, bars, hooks or other available fasteners to transmit forces to the bones or to fragments of a single bone by way of such fasteners.

It will be seen that, by the simple expedient of using a connecting component in the form of bracket 4 with screws 7 and 8, it is possible to change the combined length of the members 2 and 3, to change the angular position of the screw (fastener) 7 relative to a second fastener 114 (FIG. 1) by turning the members 2, 3 and the bracket 4 about the axis C and/or to change the angular position of the members 2, 3 simultaneously with the bracket 4 by turning these parts about the axis B. This contributes significantly to versatility of the improved apparatus.

The screw (fulcrum) 7 does not serve to pivotally connect the bracket (component) 4 to one of the force transmitting members 2 and 3. Moreover, the axis B is normal to the axis C, i.e., the angular positions of the members 2, 3 on the one hand and the bracket 4 on the other hand relative to each other can be changed by loosening the screw 8 and by thereupon turning the member 2 and the bracket 4 relative to each other about the axis C (which is normal to the axis B).

Figure 5:
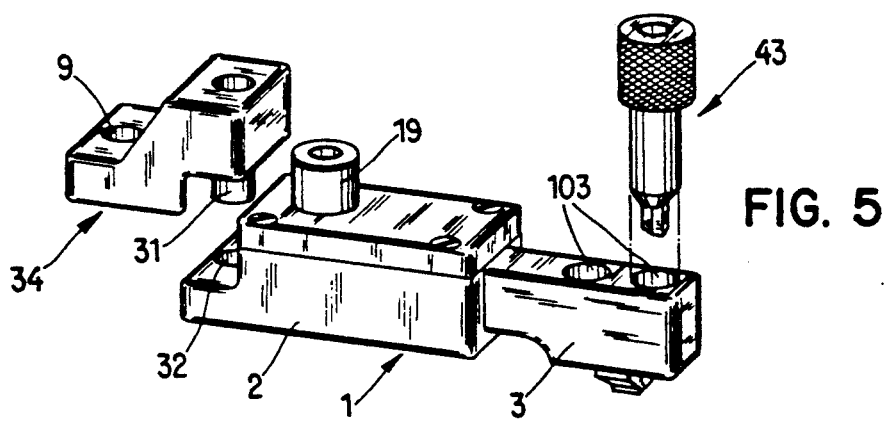
FIG. 5 is an exploded perspective view of a further apparatus with two different connecting components.

FIG. 5 shows a modification wherein a different connecting component 34 is articulately connected to the force transmitting member 2 by a pin 31 which extends into a hole or bore 32 of the member 2. The common axis of the hole 32 and pin 31 (when the pin is inserted into the hole) is parallel to the axis B, i.e., to the axis of the screw 7 (not shown in FIG. 5) which extends through the hole or bore 9 of the component 34 to connect the members 2, 3 with a plate (not shown) or directly with a bone or a fragment of a bone.

Figure 6:
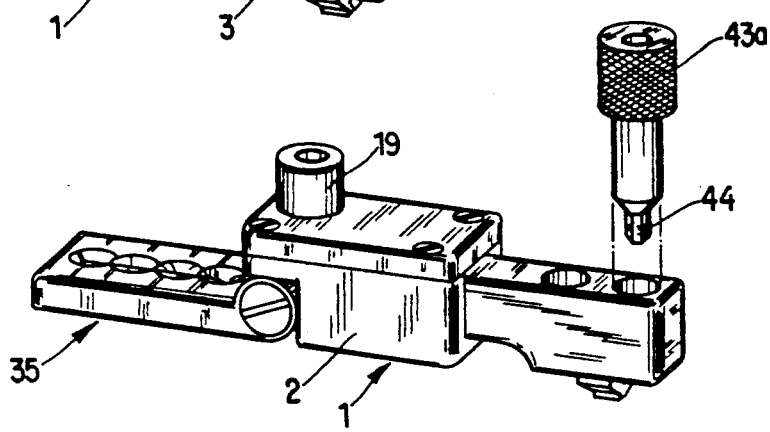
FIG. 6 is a partly exploded perspective view of an apparatus wherein the left-hand connecting component of FIG. 5 is replaced with an elongated plate-like component which is connected to one of the force transmitting members by a hinge.

A further connecting component 35, which can be used in lieu of the component 4 of FIGS. 1 and 3, is shown in FIGS. 6 to 8. The component 35 is an elongated plate which is articulately connected to the adjacent end of the force transmitting member 2 by a hinge having a pintle 38 extending at right angles to the direction of arrow A. The pintle 38 can constitute a screw which extends into a tapped bore of the member 2 so that it can be tightened in order to maintain the plate-like component 35 in a selected angular position. The connecting component 35 has an elongated slot 33 and recesses 37 for the head of a bone screw, bone pin or another suitable fastener which is to be used to secure the component 35 to a plate-like auxiliary part or directly to a bone or a bone fragment.

FIGS. 6–8 show that the plate-like component 35 has four recesses 37, i.e., a screw or the like can extend through the slot 33 in four different positions at four different distances from the pintle 38. It is clear that the number of such recesses can be reduced to one, two or three or increased to five or more. Furthermore, the recesses 37 can be omitted so that the shank of a screw or another fastener can pass through the slot 33 in any one of an infinite number of different positions, each at a different distance from the member 2.

Figure 9:
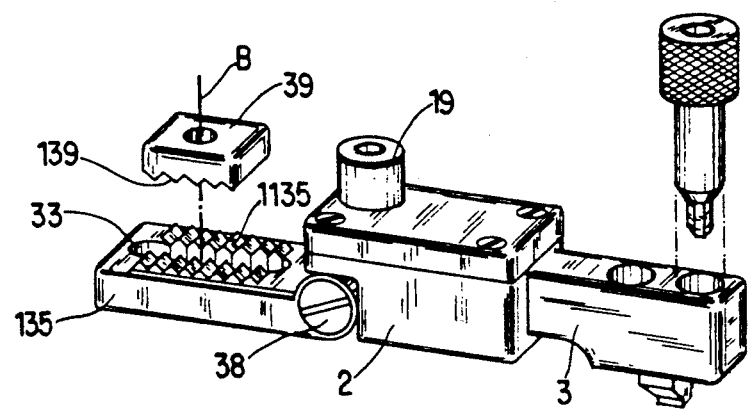
FIG. 9 is an exploded perspective view of an apparatus which constitutes a modification of the apparatus of FIGS. 6 to 8.

FIG. 9 shows a plate-like connecting component 135 which is also provided with a longitudinally extending slot 33 and is articulately connected to the adjacent end of the member 2 by a hinge including a pintle 38 extending at right angles to the direction of arrow A and constituting a screw so that the component 135 can be fixed in any desired angular position relative to the force transmitting members 2 and 3. The fastener which is used to separably secure the component 135 to a plate or to a bone or bone fragment includes a plate-like element 39 having serrations 139 which are complementary to serrations 1135 at the adjacent side of the component 135. The serrations 139 can be caused to engage selected serrations 1135 to thus locate the element 139 at a selected distance from the pintle 38. A bone screw or a like fastener is thereupon caused to extend through the centrally located hole of the element 39 and through the slot 33 to be driven into a plate, a bone or a bone fragment, not shown.

Referring again to FIG. 1, the connecting component 12 is a wheel-like or disc-shaped body which is connected directly to the adjacent end of the force transmitting member 3 by a fulcrum 11. To this end, the member 3 has a bifurcated portion with two prongs which are adjacent the end faces of the component 12 and are traversed by the fulcrum 11. The component 12 has an eccentric hole 14 (hereinafter called socket) for a portion of the fastener 114, e.g., a bone pin or the like. The apparatus 1 of FIG. 1 further comprises means (15) for releasably locking the connecting component 12 in a selected angular position. The axis of the fulcrum 11 is normal to the direction of arrow A, to the axis B and to the axis of a non-rotatable feed screw which is pivotally connected to a bearing 21 of the member 2 at one end and to a bearing 22 of the component 12 at the other end. The feed screw has two sections 40, 41 which mesh with a rotary nut 23. The nut 23 can be rotated in a clockwise direction or in a counterclockwise direction to thereby turn the component 12 about the axis of the fulcrum 11 in a desired direction and to thus change the locus of the socket 14 for the fastener 114.

The socket 14 can be provided in the fulcrum 11 if the latter is non-rotatably connected to the component 12.

FIG. 2 shows a locking means 16 which can be utilized in lieu of the locking means 15 of FIG. 1. The locking means 16 comprises a spindle 16a which is rotatable in and pivotable with a bearing 21a on the member 2 and meshes with an olive-shaped nut 22 which is non-rotatably but pivotally mounted at the periphery of the wheel-like or disc-shaped connecting component 12. One end of the spindle 16a is provided with a polygonal (e.g., hexagonal) head 16b to facilitate engagement by a standard tool, not shown. The tool can be manipulated by hand or can have a working end which is rotatable by a motor to turn the spindle 16a in a clockwise direction or in a counterclockwise direction, depending on the desired location of the socket 14.

The locking means 15 and 16 can move the connecting component 12 to a selected angular position (with reference to the axis of the fulcrum 11) to thereupon lock the component 12 in such selected position. Each of these locking means is of the self-locking type, i.e., the angular position of the component 12 will be changed only if and when the person in charge decides to rotate the nut 23 of FIG. 1 or the spindle 16a of FIG. 2.

It is often desirable to ensure that the angular position of the connecting component 12 remains unchanged when the member 3 is moved relative to the member 2 (arrow A) and/or vice versa. To this end, the member 3 can be provided with means for releasably coupling it to the locking means 15 or 16. FIG. 1 shows two arms 50 which flank the locking means 15 and are provided on the member 3. The section 40 of the feed screw can be omitted if the nut 23 is rotatably and pivotally mounted in the arms 50. The apparatus of FIG. 2 can also comprise means for releasably or permanently coupling the locking means 16 to the member 3 in such a way that the members 2, 3 can be moved relative to each other without changing the angular position of the connecting component 12 relative to the axis of the fulcrum 11.

FIGS. 3 and 4 show that the component 4 and/or 12 can be used jointly with or in lieu of a further connecting component 17 which is an elongated arm of variable length. The component 17 extends at right angles to the direction of arrow A and is detachably clamped to the force transmitting member 2 at a selected distance from the bracket 4. One end portion of the component 17 comprises two clamping jaws 24, 25 which can be secured directly to the external surface of the member 2 by a screw 26. A distancing element 27 is employed to prevent tilting of the jaws 24, 25 relative to each other. This distancing element is omitted or is replaced with a different distancing element if the person in charge decides to separably secure the jaws 24, 25 to the force transmitting member 3.

The other end of the connecting component 17 of FIGS. 3 and 4 is provided with a socket 18 for a fastener, e.g., a bone screw or a bone pin (not shown). The illustrated component 17 is assembled of two elongated sections 28 (provided with the socket 18) and 29 (integral with the jaw 25). The section 28 has an elongated slot 51 for the shank of a screw 52 serving as a means for releasably coupling the sections 28, 29 to each other in any one of a practically infinite number of different positions in each of which the socket 18 is located at a different distance from the member 2.

FIGS. 5 to 9 show that the wheel- or disc-shaped connecting component 12 can be omitted and replaced with a connecting component 43 which can extend through one of several holes 103 in the force transmitting member 3 and is provided with a polygonal (e.g., hexagonal) extension 44 at one of its ends. The extension 44 can enter a complementary socket in a bone screw (not shown) or in another fastener. The knurled head 43a of the component 43 can be rotated by hand or by resorting to a suitable tool.

The connecting component 43 can be used in lieu of or jointly with the connecting component 4, 12, 17, 34, 35 or 135.

A feature which is common to all embodiments of the improved apparatus is that the latter can carry out angular corrections in the direction of each of three axes which are disposed at right angles to each other (reference may be had to the axes B, C and to the axis of the fulcrum 11 in FIG. 1). In addition, the apparatus 1 can be used to raise or lower fragments of bones and can be used with or without fixation to a plate-like part. Thus, the apparatus can be caused to directly engage discrete bones or fragments of a bone or to engage and/or hold fasteners which are to be driven into bones or bone fragments or plates. The aforedescribed versatility and adjustability of the improved apparatus ensures that the apparatus can apply forces against the center of forces to thus avoid bending and/or other deformation of bone screws, bone pins and/or other fasteners.

The moving means 30 and the locking means 15, 16 are designed to facilitate movements of the force transmitting members 2, 3 relative to each other and/or angular movements of the connecting component 12 relative to the member 3 with a minimum of effort and with a high degree of accuracy and reproducibility. Suitable moving means can also be used to change the angular position of the plate-like component 35 or 135, to change the effective length of the component 17 and/or to change the position of any other connecting component which is used in conjunction with the members 2 and 3. The provision of a bevel gear transmission and/or other transmissions, feed screws, spindles and like parts renders it possible to shift bone fragments and/or to change the orientation of bone fragments with a high degree of accuracy. Moreover, the adjustments can be carried out within a short interval of time and with a minimum of effort. All this simplifies the task of the specialist in charge of applying the improved apparatus. The apparatus can be used for repositioning of bones or bone fragments, for changing the orientation of bones or bone fragments, to reconnect parts of a broken bone (such as a spinal column), to change the shape of a deformed bone (such as a spinal column), to ensure the restoration of broken vertebrae and/or the correction of bone fragments prior to plate fixation. All of these tasks can be carried out by changing the positions of bones or bone fragments in any one of three directions at right angles to each other or in any intermediate direction.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. An osteosynthetic fixation and force transmitting apparatus, comprising first and second force transmitting members having a common axis; means for moving said members relative to each other in a predetermined direction along said common axis; means for at least indirectly connecting said members to at least one bone, comprising a first connecting component mounted on one of said members for pivotal movement between a plurality of different positions; a fulcrum pivotally connecting said first connecting component to said one member, said fulcrum defining a predetermined axis which is substantially normal to said common axis; means for releasably locking said first connecting component in a selected position relative to said one member, said connecting means further comprising a second connecting component mounted on the other of said members for angular movement about a second axis which is normal to said direction and to said predetermined axis; and means for releasably locking said second connecting component in a selected angular position relative to said other member.

2. The apparatus of claim 1, wherein said first component comprises a bracket having a first leg and a second leg extending at right angles to said first leg and mounted on said one member, said fulcrum being connected with said first leg and further comprising a second fulcrum connecting said second leg to said one member for angular movement about an axis which is parallel to said direction.

3. The apparatus of claim 2, further comprising a second fulcrum connecting said second leg to said one member for angular movement about a third axis which is parallel to said common axis.

4. The apparatus of claim 1, wherein said second component has a socket for a bone screw or bone pin.

5. The apparatus of claim 1, further comprising means for changing the angular position of said first component, and means for releasably coupling said changing means to at least one of said members.

6. The apparatus of claim 5, wherein said means for changing the angular position of said component comprises a worm wheel drive.

7. The apparatus of claim 5, wherein said means for changing the angular position of said component comprises a rotary spindle and a nut mating with said spindle.

8. The apparatus of claim 5, wherein said means for changing the angular position of said component comprises a feed screw and a rotary nut mating with said feed screw.

9. The apparatus of claim 5, wherein said means for changing the angular position of said component includes a helical gear wheel.

10. The apparatus of claim 5, wherein said means for changing the angular position of said component is connected to each of said members.

11. The apparatus of claim 1, wherein said fulcrum is provided on said one member.

12. The apparatus of claim 1, wherein said second component extends substantially at right angles to said common axis and has a first end portion adjacent said first member and a second end portion provided with a socket for a bone screw or bone pin.

13. The apparatus of claim 12, wherein said second component comprises a plurality of sections including a first section having said first end portion and a second section having said second end portion, and means for releasably coupling said sections to each other in any one of a plurality of different positions in which said end portions are disposed at different distances from each other.

14. The apparatus of claim 12, wherein said connecting means further comprises means for securing the first end portion of said second component directly to said first member.

15. The apparatus of claim 1, wherein said connecting means further comprises devices which connect said members to bones, fragments of bones or auxiliary osteosynthetic parts independently of each other.

16. The apparatus of claim 1, further comprising means for articulately connecting said first component to said one member.

17. The apparatus of claim 16, wherein said means for articulately connecting comprises a pin-and-hole connection.

18. The apparatus of claim 1, further comprising means for securing said first component to said one member with freedom of movement about an axis which is normal to said common axis and to said predetermined axis.

19. The apparatus of claim 18, wherein said securing means comprises a hinge and said first component includes a plate having an elongated slot.

20. The apparatus of claim 19, further comprising a fastener for said plate, said plate having means for locating said fastener at any one of a plurality of different distances from said hinge.

21. An osteosynthetic fixation and force transmitting apparatus, comprising first and second force transmitting members having a common axis; means for moving said members relative to each other along said common axis; means for at least indirectly connecting said members to at least one bone, comprising a connecting component mounted on one of said members for pivotal movement between a plurality of different positions, said component comprising a bracket having a first leg and a second leg extending at right angles to said first leg and mounted on said one member; a first fulcrum pivotally connecting said first leg to said one member and defining a predetermined axis which is substantially normal to said common axis; a second fulcrum connecting said second leg to said one member for angular movement about an axis which is parallel to said direction; and means for releasably locking said connecting component in a selected position relative to said one member.

22. An osteosynthetic fixation and force transmitting apparatus, comprising first and second force transmitting members having a common axis; means for moving said members relative to each other along said common axis; means for at least indirectly connecting said members to at least one bone, comprising a connecting component mounted on one of said members for pivotal movement between a plurality of different positions; a fulcrum pivotally connecting said connecting component to said one member, said fulcrum defining a predetermined axis which is substantially normal to said common axis; means for releasably locking said connecting component in a selected position relative to said one member; and means for changing the angular position of said component, said means for changing the angular position being connected to each of said members.

* * * * *